(12) United States Patent
Faciszewski

(10) Patent No.: US 7,001,342 B2
(45) Date of Patent: Feb. 21, 2006

(54) BIOPSY/ACCESS TOOL WITH INTEGRATED BIOPSY DEVICE AND ACCESS CANNULA AND USE THEREOF

(75) Inventor: Tom Faciszewski, Marshfield, WI (US)

(73) Assignee: Movdice Holding, Inc., NV (US)

( * ) Notice: Subject to any disclaimer, the term of this patent is extended or adjusted under 35 U.S.C. 154(b) by 65 days.

(21) Appl. No.: 10/074,512

(22) Filed: Feb. 11, 2002

(65) Prior Publication Data

US 2003/0083592 A1 May 1, 2003

Related U.S. Application Data

(63) Continuation-in-part of application No. 10/017,770, filed on Oct. 30, 2001.

(51) Int. Cl.
A61B 5/04 (2006.01)

(52) U.S. Cl. ...................................... 600/564
(58) Field of Classification Search ......... 600/562–567; 604/164.01, 164.03, 164.09, 164.1–165.01
See application file for complete search history.

(56) References Cited

U.S. PATENT DOCUMENTS

| | | |
|---|---|---|
| 4,487,209 A | 12/1984 | Mehl |
| 5,236,334 A | 8/1993 | Bennett |
| 5,415,812 A | 5/1995 | Durbut et al. |
| 5,462,062 A | 10/1995 | Rubinstein et al. |
| 5,477,862 A | 12/1995 | Haaga |
| 5,522,398 A | 6/1996 | Goldenberg et al. |
| 5,595,186 A | 1/1997 | Rubinstein et al. |
| 5,954,671 A * | 9/1999 | O'Neill ...................... 600/567 |
| 5,964,761 A | 10/1999 | Kambin |
| 6,015,391 A | 1/2000 | Rishton et al. |
| 6,110,128 A | 8/2000 | Andelin et al. |
| 6,221,029 B1 | 4/2001 | Mathis et al. |
| 6,447,477 B1 | 9/2002 | Burney et al. |
| 6,468,279 B1 | 10/2002 | Reo |
| 2003/0004530 A1 | 1/2003 | Reo |

FOREIGN PATENT DOCUMENTS

| | | |
|---|---|---|
| EP | 1074231 | 2/2001 |
| WO | WO 00/56220 | 9/2000 |

* cited by examiner

*Primary Examiner*—Max Hindenburg
(74) *Attorney, Agent, or Firm*—Stephen Faciszewski

(57) ABSTRACT

Method of use for a biopsy/access tool, comprising an integrated biopsy device and access cannula. In this method, the biopsy device is internally guided to a remote anatomical site, and the access cannula is adapted to be guided to the same remote anatomical body site by the biopsy device.

6 Claims, 9 Drawing Sheets

BIOPSY/ACCESS TOOL WITH INTEGRATED BIOPSY DEVICE AND ACCESS CANNULA AND USE THEREOF

This application is a Continuation-in-Part application of U.S. application Ser. No. 10/017,770, filed Oct. 30, 2001.

BACKGROUND OF THE INVENTION

1. Field of the Invention

The present invention relates generally to surgical devices and methods, methods for harvesting specimens and accessing remote anatomical sites, more specifically to biopsy devices integrated with access cannulae and methods of use thereof.

2. Description of the Related Art

Various biopsy devices and access cannulae are known in the art. Typically, these devices are configured to work independently of one another, and are not designed to work in concert so as to allow the precise retrieval of a biopsy specimen relative to placement of an access cannula.

In certain surgical procedures such as vertebroplasty, endoscopy, laparoscopy, and arthroscopy, an access cannula is used to establish a pathway to a remote operative site in the body. Often the operative site is surrounded by critical neurovascular structures that must be protected from iatragenic compromise. It would therefore be an advantage over the prior art to have an integrated access tool and biopsy device that function in concert with one another to minimize tissue trauma, and more importantly, maintain a tract to the remote operative site. It would be a further advantage over the prior art to have a guided biopsy device for harvesting tissue from a remote internal body site.

For example, the state of the art provides biopsy tools that work independently of access cannulas. An example of known biopsy tools is shown in U.S. Pat. No. 5,595,186, issued Jan. 21, 1997, to Rubinstein, et al. or U.S. Pat. No. 4,487,209, issued Dec. 11, 1984, to Mehl. In addition, European Patent No. 1074231, granted Feb. 7, 2001, to Al-Assir represents a surgical technique using an access cannula.

Unfortunately, conventional practices require first establishing a tract to the remote operative site with a biopsy tool. After harvesting a specimen and removing the biopsy tool, the tract to the remote operative site must then be re-established when positioning a cannula, causing additional trauma to intervening tissue (particularly if positioning the cannula creates a different access tract) and risking injury to vital anatomical structures adjacent to or in the cannula access path.

Additionally, it is often desirable to locate the tract to a remote operative site with a small guide wire under fluoroscopic visualization. After the guide wire tract is established, larger tools can be placed over the guide wire and advanced along the "guided" path to the operative site. It would be an improvement over the prior art to provide a biopsy device that is guided over a wire or rod to reach a remote operative site with minimal disruption or trauma to the adjacent tissue. It would be a further improvement to provide a cannula that is guided into position by a biopsy device to maintain the tract previously established to the remote operative site by the biopsy device and minimize the number of steps required to carry out the surgical procedure.

SUMMARY OF THE INVENTION

One aspect of the present invention is an integrated biopsy/access tool for harvesting a biopsy specimen and provides access to a remote anatomical site. The inventive biopsy/access tool comprises: i) a biopsy device having distal and proximal ends; ii) a cannula having distal and proximal ends, and a first functional channel extending therebetween; and iii) a handle means, removably coupled to at least one of the biopsy device and cannula.

In the inventive biopsy/access device, if the handle means is separated from the biopsy device, at least a portion of the first functional channel is capable of telescoping over the biopsy device. Preferred, inventive cannulae may have a distal tip adapted to gently displace tissue outward (thereby avoiding tissue trauma) as a cannula is advanced over a biopsy device. Although alternative embodiments are disclosed herein, generally, when the cannula is completely advanced over the biopsy device, the distal ends of the biopsy device and cannula may be aligned.

The invention also comprises a method for obtaining a biopsy specimen, accessing a remote anatomical site, or both. In the inventive method one places a biopsy device at an anatomical site; advances a cannula over the biopsy device; secures the biopsy specimen; and withdraws the biopsy device containing the biopsy specimen, thereby providing access to a remote anatomical site without having to re-establish a cannula tract. Although skilled artisans will appreciate various procedural alternatives, in a preferred inventive method, prior to placing the biopsy device, one may position a placement means at the remote anatomical site. The inventive method may employ any of the inventive placement means contemplated herein. In a further exemplary method, one advances a trocar through the skin to a remote anatomical site. The trocar proximal end may preferably be adapted to receive a handle prior to placement of the trocar. The connection between the trocar and the trocar handle is adapted to transmit compression and torque, thus facilitating/advancing the distal end of the trocar to the remote anatomical site. The trocar may be cannulated so as to advance over a guide wire first placed at the remote anatomical site. After final placement of the trocar, the guidewire and handle are removed.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein.

DETAILED DESCRIPTION OF THE PREFERRED EMBODIMENTS

Figure 1:
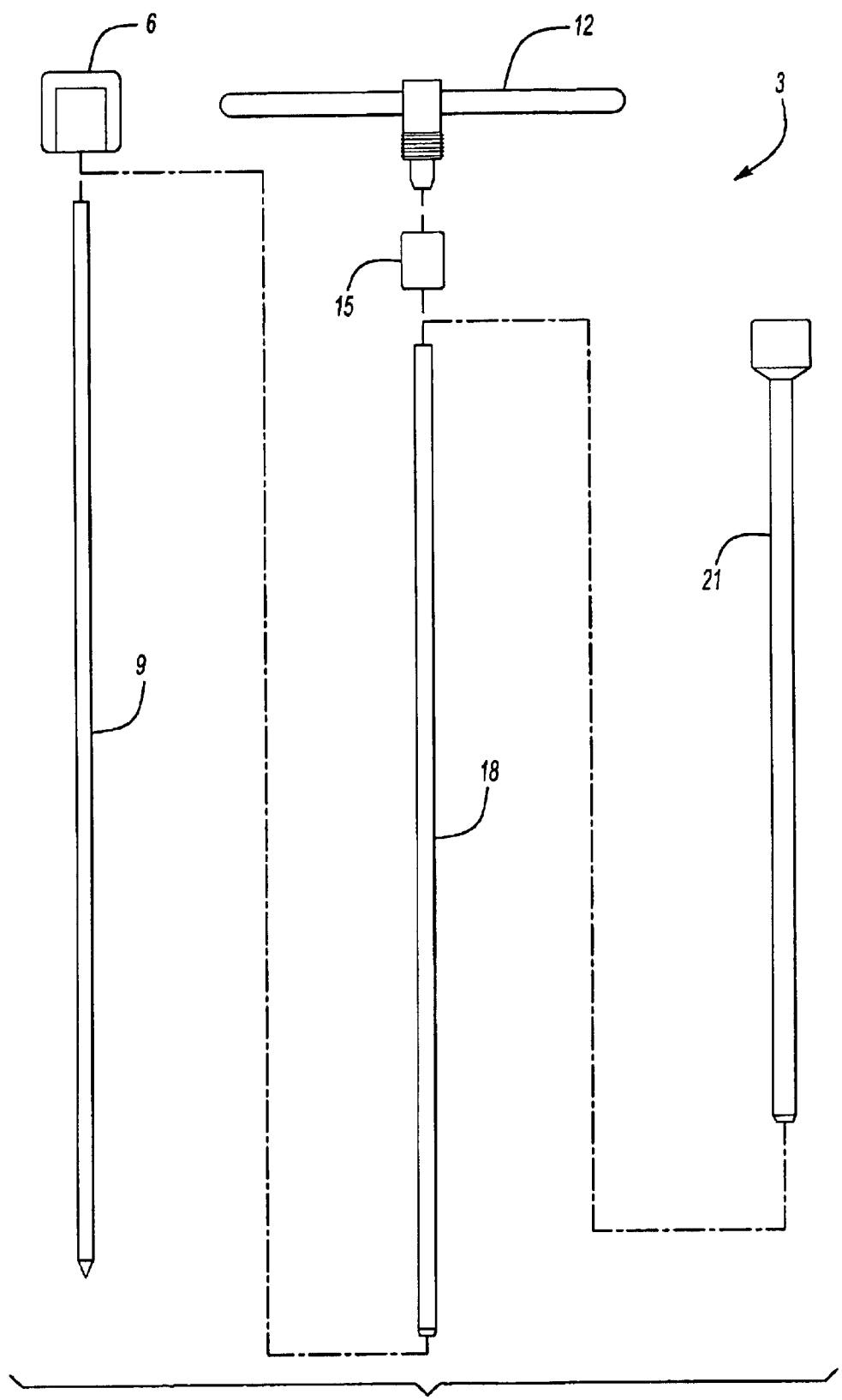
FIG. 1 is an exploded view of a preferred embodiment of an inventive biopsy/access tool.

In a preferred embodiment, when the cannula distal end is disposed relative to the biopsy specimen or anatomical site and the biopsy device advanced within said channel such that a handle distal end engages the cannula proximal end, the biopsy device distal end extends a distance beyond said cannula distal end, thereby securing a biopsy specimen.

Although a wide range of dimensions are within the scope of the invention, preferably, the biopsy device has an outer dimension ranging from 2 to 3 millimeters, and the cannula has an outer dimension between 3 and 4 millimeters. Depending on the intended use for a biopsy/cannula tool according to the invention, components of the tool will typically range in size, such as the, non-limiting, exemplary ranges shown in Table 1, below.

TABLE 1*

| COMPONENT | SMALL | LARGE |
| --- | --- | --- |
| Trocar | 1.0 mm ID / 2.0 mm OD | 1.5 mm ID / 3.0 mm OD |
| Biopsy Device | 2.0 mm ID / 3.0 mm OD | 3.0 mm ID / 4.0 mm OD |
| Cannula | 3.0 mm ID / 4.0 mm OD | 4.0 mm ID / 5.0 mm OD |

*ID is inside diameter, and OD is outside diameter.

In addition, preferred biopsy devices may comprise a means for securing a biopsy. Such securing means operate to sever and retain the biopsy specimen, specifically a cutting tooth, as for example, is disclosed in Australian Patent No. 200033065, granted Oct. 9, 2000, to Cervi, or U.S. Pat. Nos. 5,477,862, and 5,462,062, issued Dec. 26, 1995, and Oct. 31, 1995, to Haaga and Rubinstein, et al., respectively.

A preferred biopsy/access tool further comprises a placement means for determining proper placement or the biopsy device (e.g., measuring a penetration depth of any one of the biopsy/access tool, biopsy device, cannula or both at the remote anatomical site). The handle means may be removably coupled to the placement means. The placement means may be a trocar, a guide wire, or a linear scale. The trocar may, but not necessarily, be solid, cannulated (for placement over a guide wire), have a tapered distal end, an outer dimension between 2 and 3 millimeters, and a channel extending therethrough. In a preferred embodiment, the placement means (e.g. the trocar) is telescopically received within a second functional channel extending through the biopsy device.

In any of the inventive embodiments, tolerance between the placement means, biopsy device and cannula is small enough that tissue does not become wedged therebetween. A representative tolerance between an outer dimension of a placement means or biopsy device and an outer dimension of a biopsy device and cannula, respectively, preferably ranges from 0.02 to 0.3 mm, more preferably from 0.02 to 0.03 mm. Although thickness of a guide wire according to the invention may vary considerably, the guide wire preferably has a thickness of from 1.0 to 3.0 mm, more preferably 1.5 mm.

A representative, preferred linear scale according to the invention may be one or more axially-spaced demarcations on the biopsy device or cannula. Employing this exemplary linear scale, when the cannula distal end is disposed relative to the biopsy specimen or anatomical site, and the biopsy device is advanced through the first functional channel, aligning a demarcation with the cannula proximal end, then the biopsy device distal end extends a predetermined distance beyond said cannula distal end, thereby positioning the biopsy device for securing the biopsy specimen.

In an alternative placement means, the biopsy device may have a distally-facing surface distal to its proximal end, and the cannula may have a proximally-facing surface proximate to its proximal end. In operation of this alternative embodiment, when the biopsy device's distally-facing surface engages the cannula's proximally-facing surface, the distal tip of the biopsy device will extend a predetermined distance beyond the distal tip of the cannula, so as to secure an adequate length of tissue specimen.

In an alternative embodiment of the invention, the handle means simultaneously couples proximal ends of the biopsy device and cannula. In operating this inventive embodiment, one may place the resulting coupled assembly over the placement means (e.g., the trocar), release the handle means from the cannula, and further advance the biopsy device relative to the cannula to secure the tissue specimen. Or, either the biopsy device, cannula or both may further comprise a leuer-type coupler, the leuer-type coupler being removably coupled to the biopsy device or cannula and capable of removably coupling to the handle means.

A preferred handle means according to the invention may comprise one or more grip means, the grip means removeably coupled to the biopsy device, cannula, placement means, or all (or any combination of) the foregoing. A preferred grip according to the invention comprises a threaded member having threads that engage proximal threads of the biopsy device, cannula or placement means. In a more preferred embodiment, a first grip removably couples with the biopsy device, and a second grip removably couples to the cannula.

In some instances, the inventive biopsy/access tool comprises a trocar, a trocar handle, a biopsy device, a biopsy handle, and a cannula.

Again, the biopsy device, further adapted to be releasably connected to a biopsy handle, may have a second functional channel for telescopically receiving an outside surface of the trocar. After attaching a handle to the biopsy device, the biopsy device is placed over the trocar and advanced along the trocar so that the biopsy device and trocar distal ends are generally aligned. So as to minimize tissue trauma during advancement of the biopsy device, the biopsy device distal tip may be tapered to gently displace tissue outward as the biopsy device is directed over the trocar toward a remote anatomical site. Upon final placement of the biopsy device at a remote anatomical site, the biopsy handle and trocar may be removed, more preferably, one attaches an extension to the biopsy device, thereby preventing its subsequent displacement.

In the inventive method, one may couple a handle means to a cannula and slide the coupled cannula telescopically over the biopsy device to advance the cannula. In addition, although skilled artisans may appreciate modified method steps, one may secure a biopsy specimen by coupling a handle means to the biopsy device; advancing the coupled biopsy device; and fixing a biopsy specimen in the biopsy device with a securing means, the securing means severing and retaining the biopsy specimen.

The inventive method most notably provides access to a remote anatomical site for introducing, for example, devices, tools, instruments, medicaments, biomaterials and other matter, such as, without limitation, a delivery cannula, tissue modification devices, catheters, tubes, diagnostic instruments, and pharmaceuticals and therapeutic agents. In preferred, alternative methods according to the invention, one places at the remote anatomical site, through the cannula, one or more delivery cannulae; advances a push rod through the delivery cannula, thereby depositing a pharmaceutical or therapeutic agent contained in the delivery cannula at the remote anatomical site; and removes the delivery cannula.

Non-exhaustive and representative: i) tissue modification devices may be mechanical or pressure devices for displacing or modifying tissue; ii) diagnostic instruments may be video-assisted endoscopes and ultrasound probes; and ii) pharmaceuticals and therapeutic agents may be polymethylmethacrylate, bone growth factors, and calcium hydroxy-apatite substances.

Looking first at FIG. 1, there is shown a biopsy/access tool 3 comprising a trocar handle 6, a trocar 9, a biopsy handle 12, a locking nut 15, a biopsy device 18, and a cannula 21. The trocar handle releasably attaches to the trocar. The trocar handle 6 has a non-circular recess 24 (FIG. 2C) that connects to a corresponding shape on the proximal end 27 (FIGS. 2C and 2D) of the trocar so that torque and compression can be transmitted from the handle 6 to the trocar 9. The trocar 9 is sized so as to be telescopically received within the biopsy handle 12 and biopsy device 18. The biopsy handle 12 has a split collet configuration 30 (FIG. 4C) on its distal end and is connected to the biopsy device 18 by means of the locking nut 15 that compresses the split collet 30 against the outside surface of the biopsy device 18. As will hereinafter be discussed, biopsy device 18 is sized to be telescopically received in the central lumen of cannula 21.

Figure 2A:
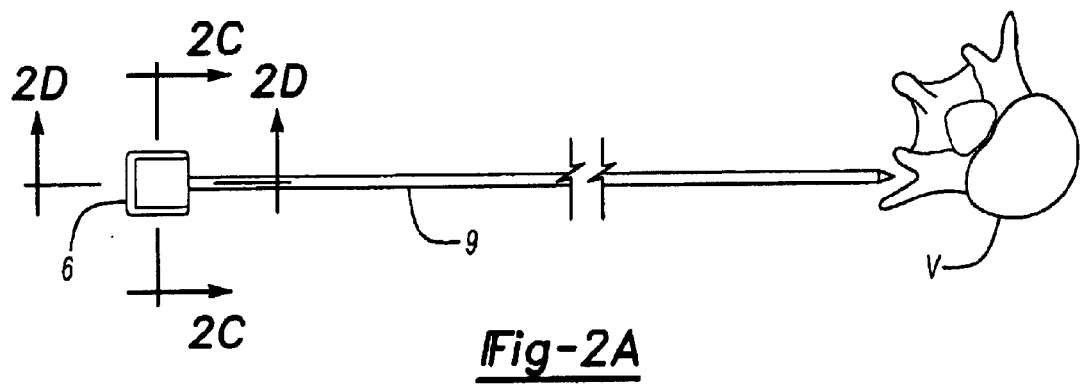
FIG. 2A is a top view showing a vertebra, trocar and trocar handle in a first operative position.
Figure 2B:
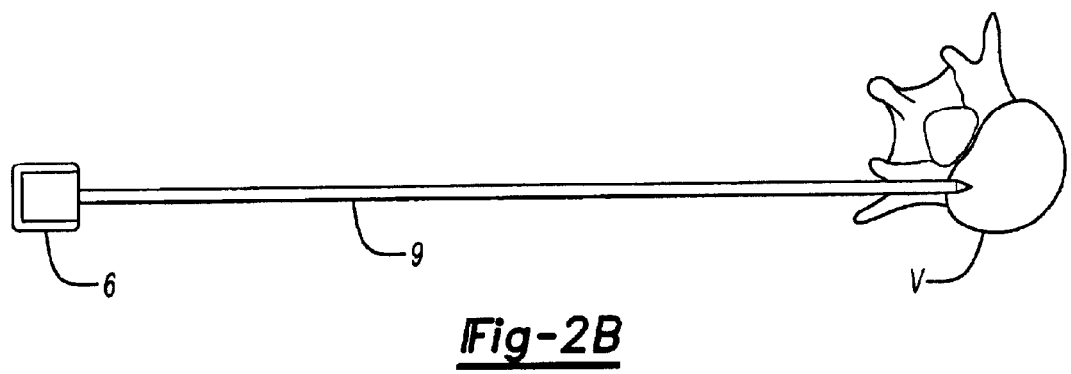
FIG. 2B is a top view of the vertebra and trocar in a second operative position.

FIGS. 2A and 2B show the approach and placement, respectively, of the trocar 9 into a tissue mass. For purposes of illustration, the tissue mass discussed herein is characterized as a vertebra V, but the methods and devices disclosed herein may be used in connection with any soft or hard tissue mass.

Figure 2C:
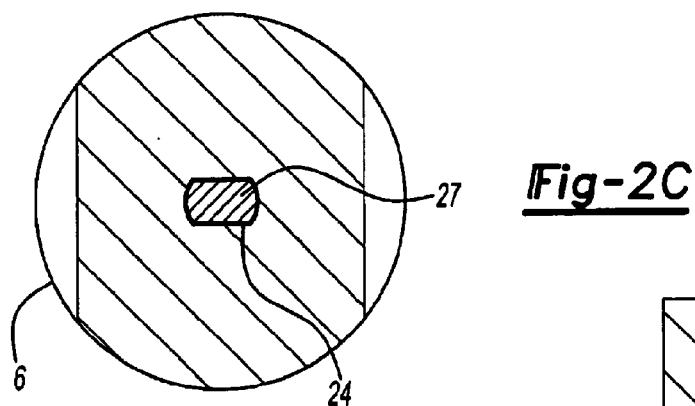
FIG. 2C is a transverse sectional view of the trocar handle shown in 2A, taken along the line 2C—2C of FIG. 2A.
Figure 2D:
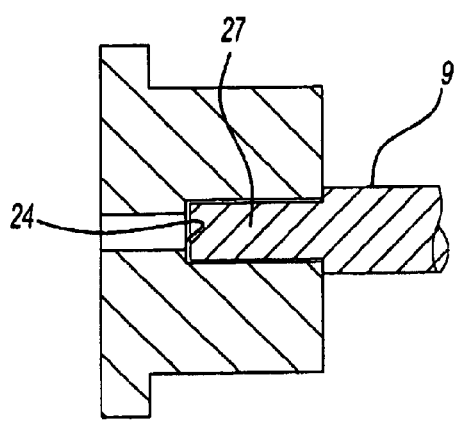
FIG. 2D is a longitudinal sectional view of the trocar handle shown in 2A, taken along the line 2D—2D of FIG. 2A.

FIG. 2C is a sectional view of the trocar handle 6 and trocar 9 shown in FIG. 2A and, in conjunction with FIG. 2D, show how trocar handle 6 may be removably attached to trocar 9 so that torque and compression can be transmitted from handle 6 to trocar 9, whereby trocar 9 can be advanced into vertebra V (FIGS. 2A and 2B).

Figure 3A:
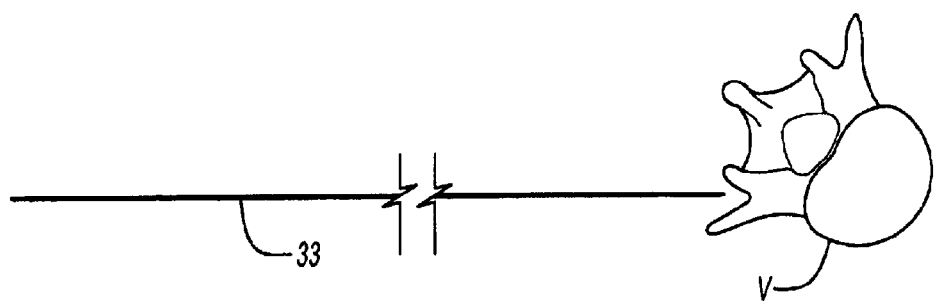
FIG. 3A is a top view of a vertebra and guide wire in a first operative position.
Figure 3B:
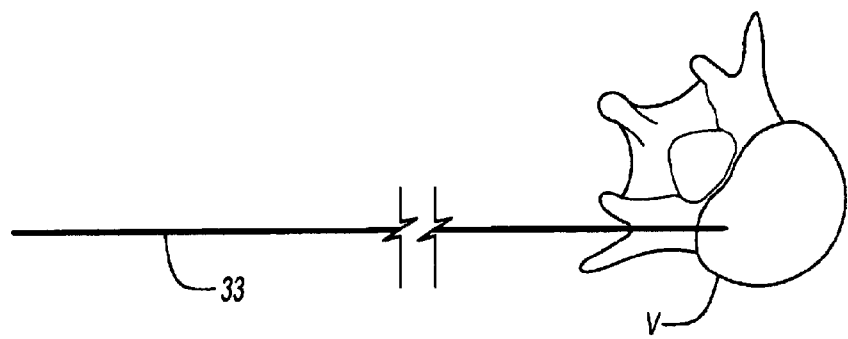
FIG. 3B is a top view of the vertebra and guide wire in a second operative position.
Figure 3C:
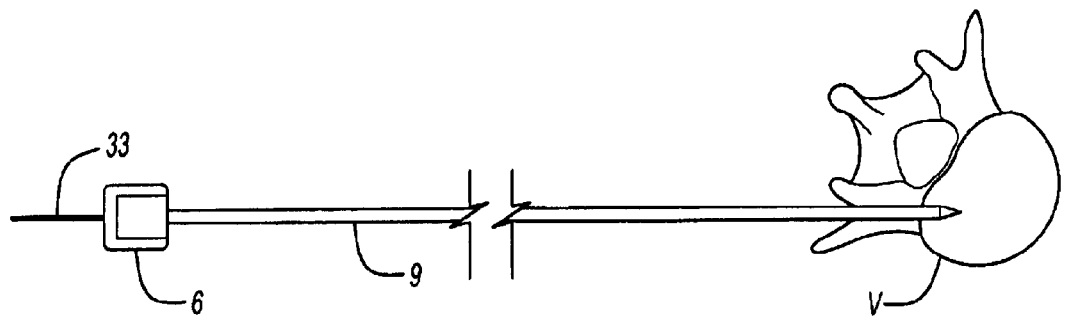
FIG. 3C is a top view of a vertebra, a guide wire, trocar and trocar handle.
Figure 3D:
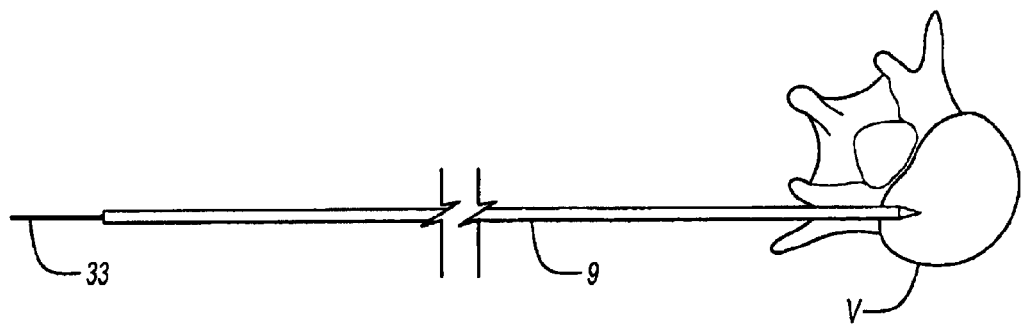
FIG. 3D is a top view of the vertebra, guide wire, and trocar.

FIGS. 3A, 3B, 3C, and 3D show an alternate technique for the approach and placement of the trocar into vertebra V. More particularly, FIGS. 3A and 3B first show the approach and placement of a guidewire 33 into vertebra V, followed by the placement of the cannulated trocar 9 (with the trocar handle 6 attached) over the guidewire 33 as shown in FIG. 3C. Then the trocar handle 6 is removed (FIG. 3D), and then guidewire 33 is withdrawn leaving just trocar 9 extending into vertebra V.

Figure 4A:
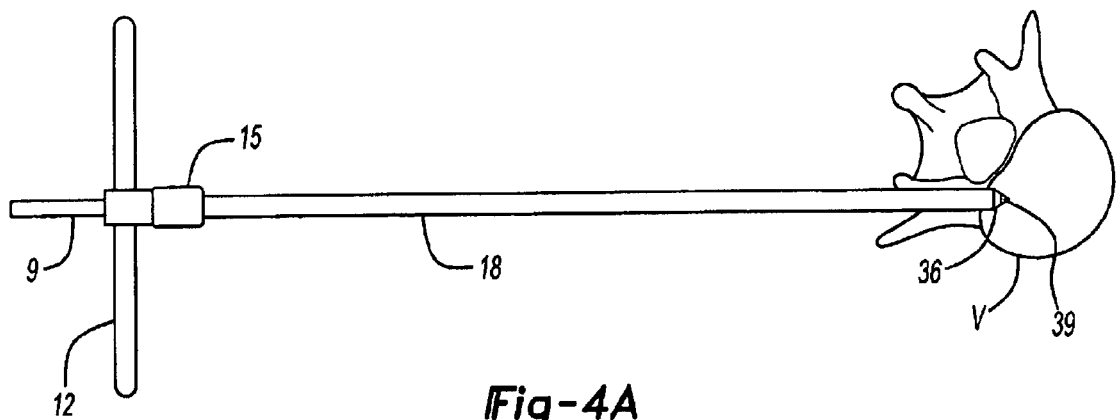
FIG. 4A is a top view of a vertebra, biopsy device, removable biopsy handle, and trocar.
Figure 4B:
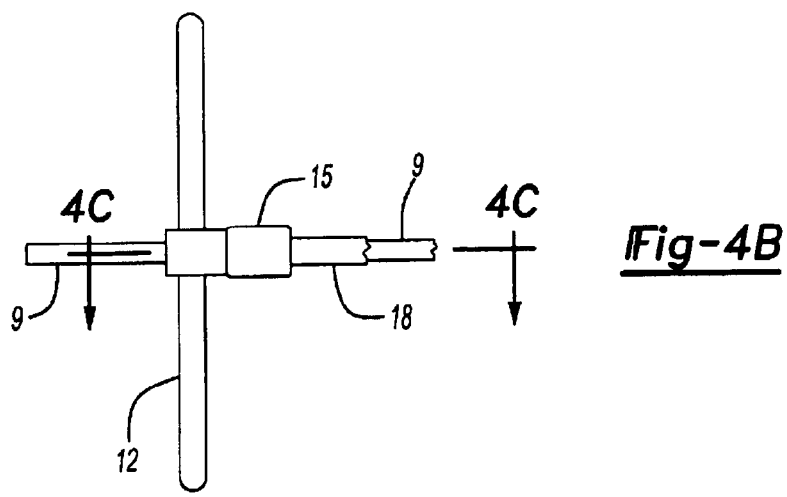
FIG. 4B is a close-up view of selected portions of a preferred biopsy device, removable biopsy handle, and trocar.
Figure 4C:
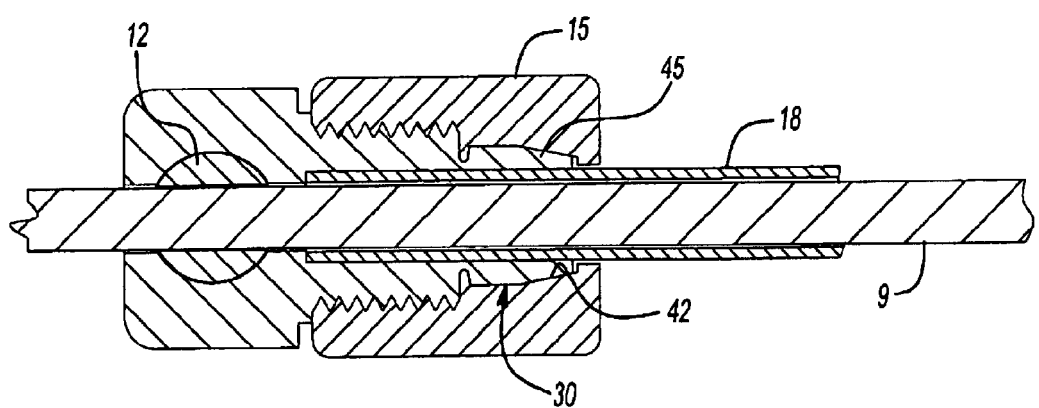
FIG. 4C is a sectional view taken along line 4C—4C of FIG. 4B.

FIG. 4A shows the biopsy device 18 advanced over the trocar 9, with the distal tip 36 of the biopsy device advanced to the distal tip 39 of the trocar. FIG. 4B shows a close-up veiw of selected portions of FIG. 4A, where the trocar 9 extends proximal to the proximal end of the biopsy removable handle 12. FIG. 4C is a sectional view taken along line 4C—4C of FIG. 4B, illustrating how an internal taper 42 on the locking nut 15 contacts an external taper 45 on the biopsy removable handle 12, causing the split collet 30 on the distal end of the biopsy removable handle to compress and secure the biopsy device 18.

Figure 5:
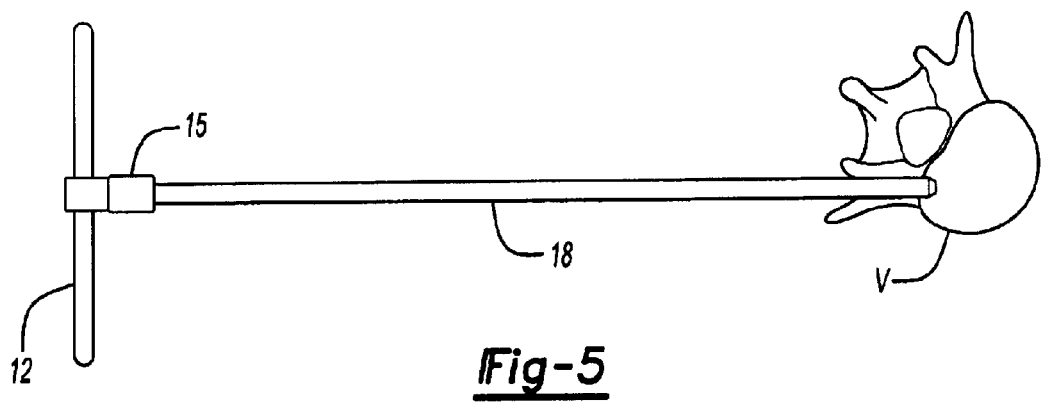
FIG. 5 is a top view of a vertebra, biopsy device and removable biopsy handle.

FIG. 5 shows the biopsy device 18 (with the biopsy handle 12 attached) after the trocar 9 has been removed.

Figure 6:
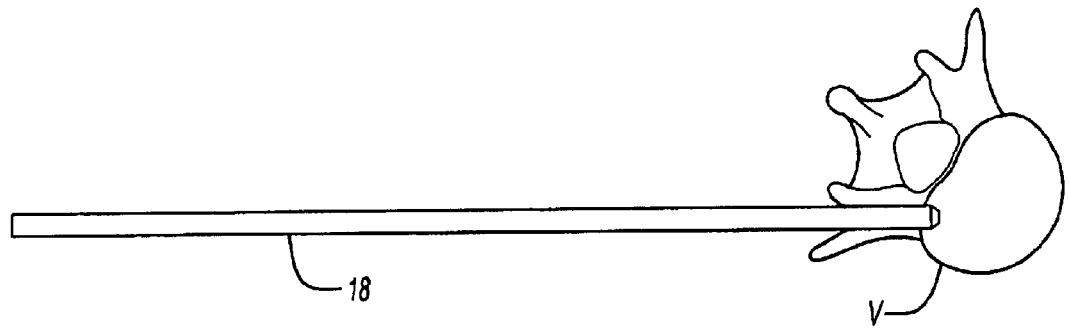
FIG. 6 is a top view of a vertebra and biopsy device.

FIG. 6 shows the biopsy handle 12 removed from the biopsy device 18.

Figure 7A:
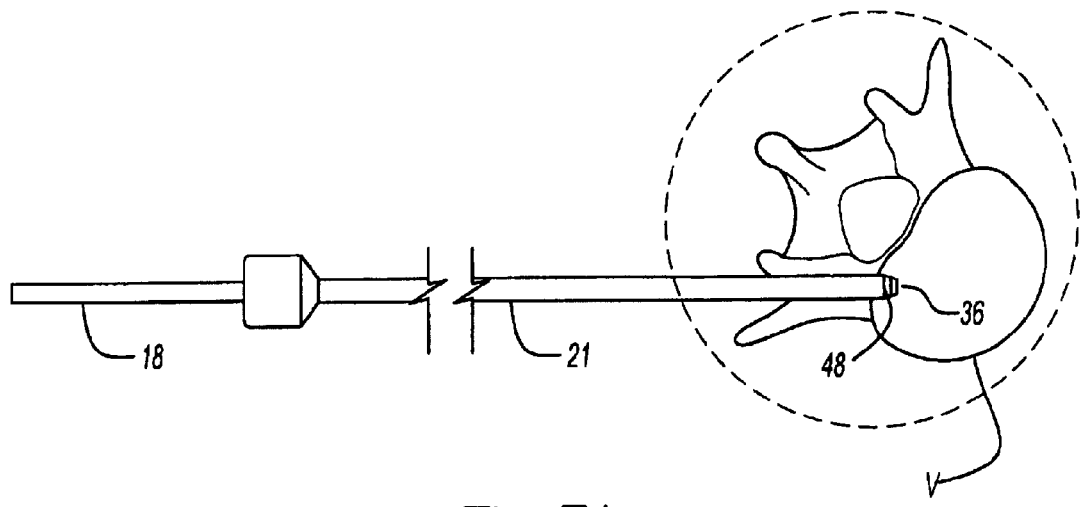
FIG. 7A is a top view of a vertebra, biopsy device and cannula.
Figure 7B:
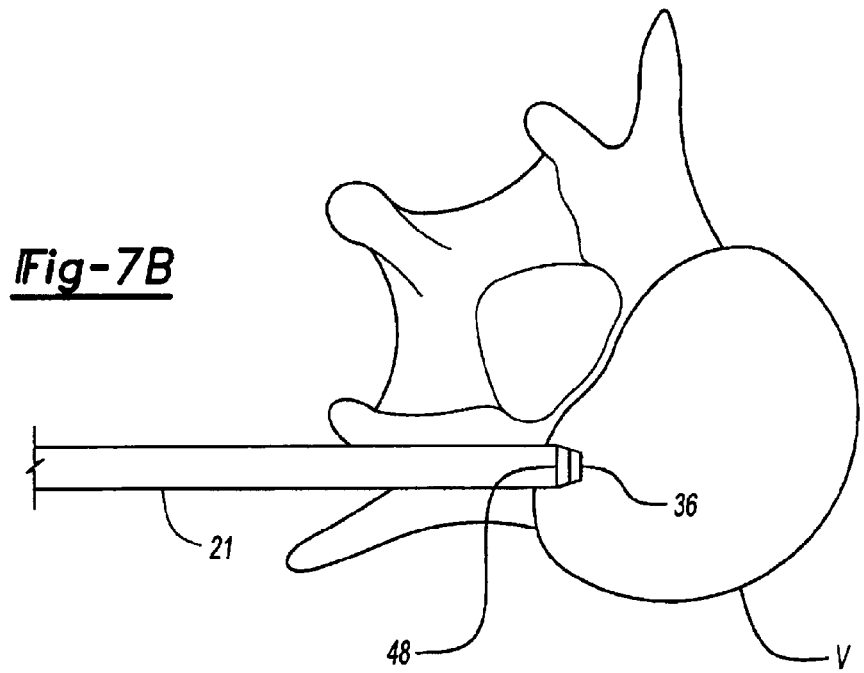
FIG. 7B is a close-up view of the elements circled in FIG. 7A.

FIG. 7A shows the cannula 21 advanced over the biopsy device 18, with the distal end 48 of the cannula 21 aligned with the distal end 36 of the biopsy device 18 as shown in FIG. 7B.

Figure 8A:
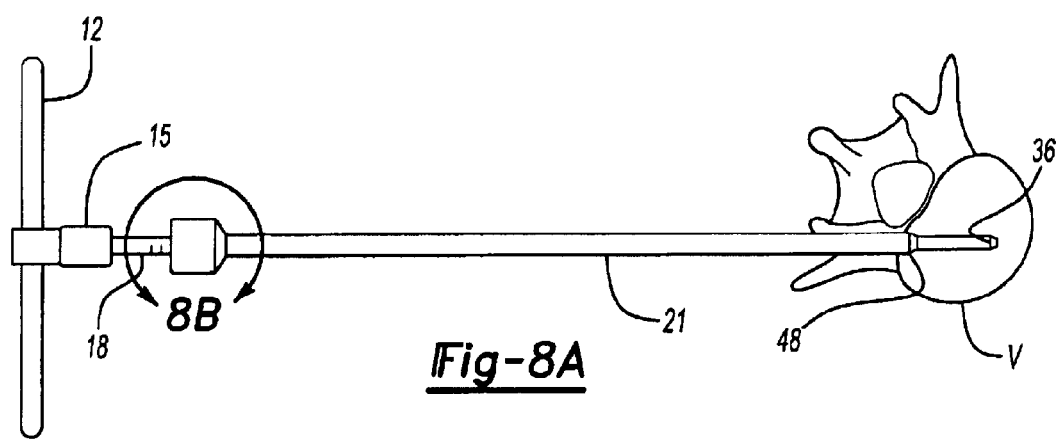
FIG. 8A is a top view of a vertebra, the biopsy device, removable biopsy handle and cannula.
Figure 8B:
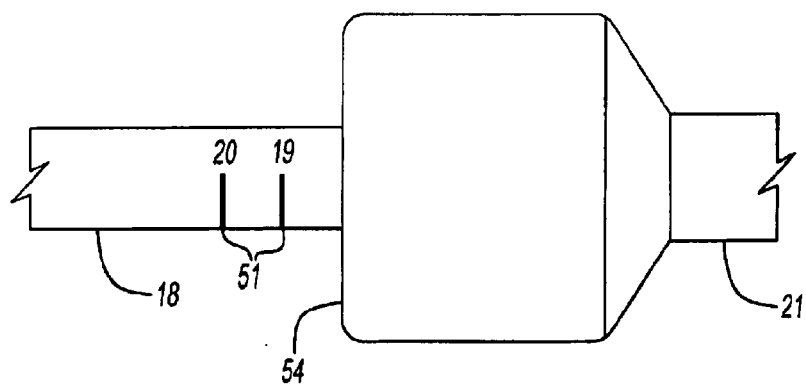
FIG. 8B is a close-up view of the elements circled in FIG. 8A.

FIG. 8 shows the biopsy handle 12 reattached to the biopsy device 18, and the distal tip 36 of biopsy device 18 advanced a predetermined distance beyond the distal end 48 of the cannula 21 so as to harvest the desired tissue specimen from vertebra V. At this point the biopsy specimen is secured within the internal cavity of the biopsy device.

In order to regulate the extent to which the distal tip 36 of biopsy device 18 extends beyond the distal tip 48 of cannula 21 (i.e., in order to regulate the penetration of biopsy device 18 into vertebra V), biopsy device 18 may include axially spaced demarcations 51 (FIG. 8B) on its external surface for referencing against the proximal end 54 of cannula 20.

Figure 9:
FIG. 9 is a top view of a vertebra and cannula.

FIG. 9 shows the cannula 21 with the biopsy device 18 removed. At this point, a subsequent surgical procedure can begin. The cannula 21 can then serve as a working channel for safely advancing operative tools to vertebra V, or for delivering therapeutic agents or biomaterials or diagnostic instruments to vertebra V.

Figure 10:
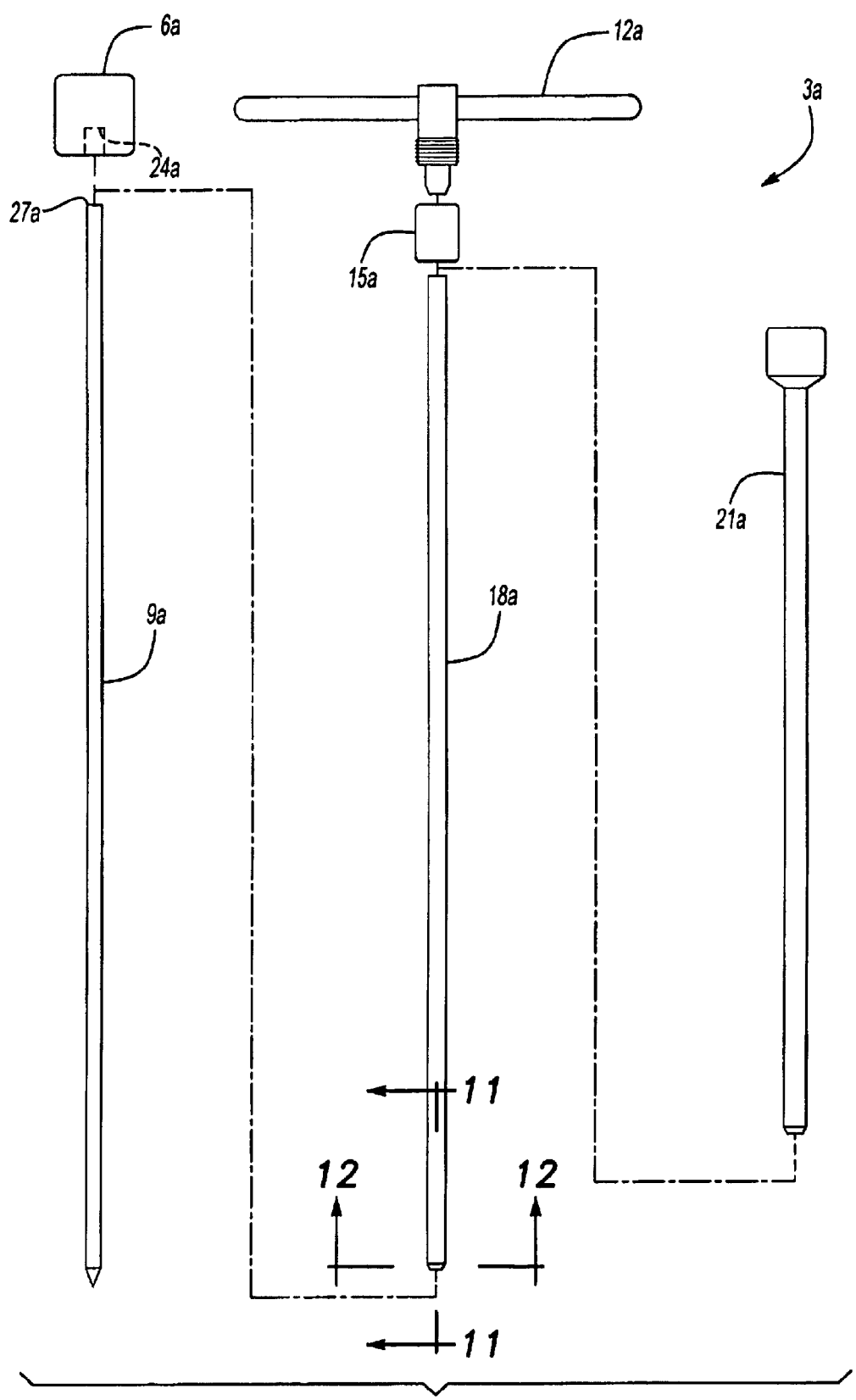
FIG. 10 is an exploded view of an alternative biopsy/access tool embodiment of the invention.

Considering FIG. 10, there is shown a biopsy/access tool 3A comprising a trocar handle 6A, trocar 9A, biopsy handle 12A, locking nut 15A, biopsy device 18A, and cannula 21A. The trocar handle 6A attaches to the trocar 9A. The trocar handle 6A has a non-circular recess 24A (FIG. 10) that connects to a corresponding shape on the proximal end 27A of the trocar 9A so that torque and compression can be transmitted from the handle to the trocar. The trocar 9A is sized so at to to be telescopically received within the biopsy handle 12A and biopsy device 18A. The biopsy device 18A has a distal biopsy securing means 60A (FIGS. 11 and 12) to aid the retrieval of a biopsy specimen. The biopsy handle 12A has a split collet configuration (not shown in FIGS. 10–14) at its distal end and the biopsy handle 12A is connected to the biopsy device 18A by means of the locking nut 15A that compresses the split collet onto the outer surface of the biopsy device. The biopsy device 18A is sized so as to be telescopically received in the central lumen (functional channel) of cannula 21A.

Figure 11:
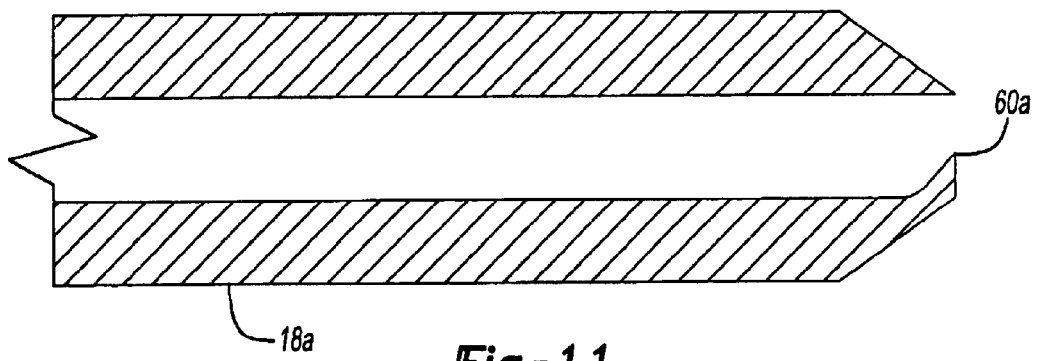
FIG. 11 is a sectional view of the biopsy device, taken along the line A—A of FIG. 10.
Figure 12:
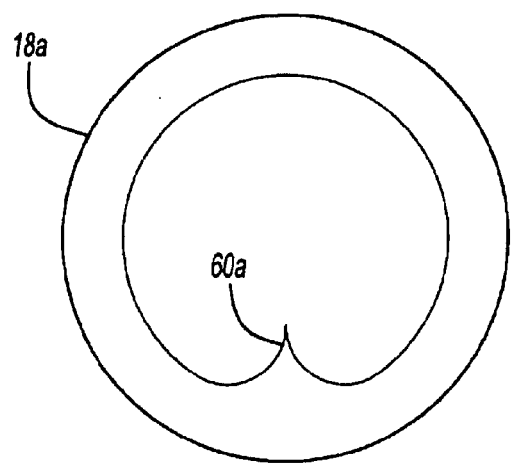
FIG. 12 is an end view of the biopsy device shown in FIG. 11.

FIG. 11 shows a cross section of the distal end of the biopsy device 18A, illustrating a distal biopsy securing means 60A in cross-section. FIG. 12 is an end view of the distal end of the biopsy device, illustrating an end view of the distal biopsy securing means 60A.

Figure 13A:
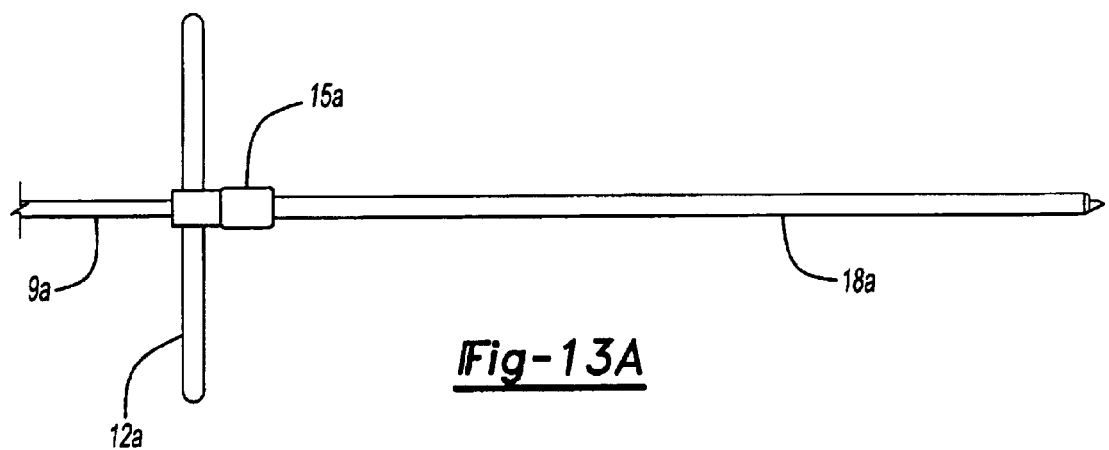
FIG. 13A is a side view of a biopsy device, biopsy handle and trocar.
Figure 13B:
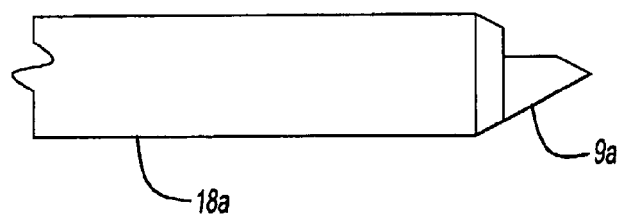
FIG. 13B is a close-up view of selected portions of the trocar and biopsy device shown in FIG. 13A.

FIG. 13A shows the biopsy device 9A (with the biopsy handle 12A attached) assembled to the trocar 9A, and FIG. 13B is a close-up view of the distal ends of trocar 9A and biopsy device 18A.

Figure 14:
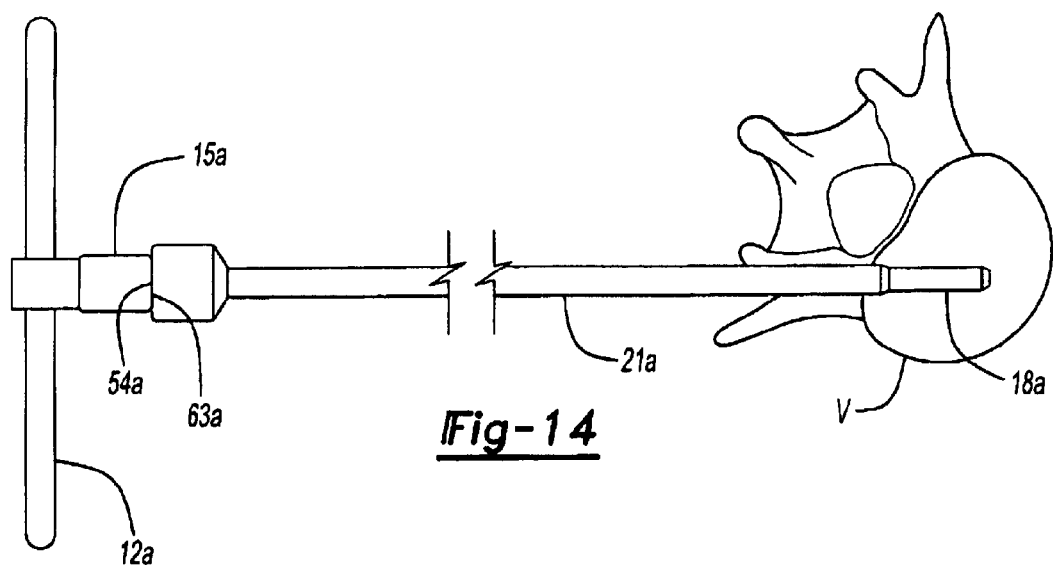
FIG. 14 is a top view of a vertebra, biopsy device, biopsy handle, and cannula.

FIG. 14 shows a vertebra V with the biopsy device 18A and cannula 21A in place, where the biopsy device 18A is advanced until the distal surface 63A of the locking nut contacts the proximal end 54A of the cannula, thereby precisely determining the depth of penetration of the biopsy device into the tissue mass.

The biopsy/access tool shown in FIG. 10 is used in a method analogous to the methods illustrated in FIGS. 2–9, with the following two exceptions.

First, the precision control of the depth of biopsy device penetration beyond the cannula is different, as illustrated in FIG. 14. The locking nut 15A attached to the biopsy handle 12A presents a distally-facing surface 54A that is configured to contact the proximally-facing surface 63A of the proximal end of the cannula when a predetermined length of the biopsy device extends beyond the distal end of the cannula.

Second, once the biopsy device has been advanced to the proper depth as shown in FIG. 14, the biopsy device 18A is rotated 360 degrees so as to score the distal end of the biopsy specimen with the biopsy securing means 60A. Then the biopsy device 18A is removed with the tissue specimen.

What is claimed is:

1. A method for obtaining a biopsy specimen and accessing a remote anatomical site, comprising the steps of:
    a. placing a biopsy device at an anatomical site;
    b. advancing a cannula over the biopsy device;
    c. securing the biopsy specimen; and
    d. withdrawing the biopsy device containing the biopsy specimen from the remote anatomical site, thereby providing access through the cannula to the remote anatomical site.

2. The method according to claim 1, further comprising the step of positioning a placement means at the remote anatomical site prior to placing the biopsy device.

3. The method according to claim 1, wherein advancing the cannula comprises the steps of:
    a. coupling a handle means to a cannula; and
    b. sliding the cannula coupled to the handle telescopically over the biopsy device.

4. The method according to claim 1, wherein securing the biopsy specimen comprises the steps of:
    a. coupling a handle means to the biopsy device;
    b. advancing the biopsy device; and
    c. fixing a biopsy specimen in the biopsy device with a securing means.

5. The method according to claim 4, wherein the securing means severs and retains the biopsy specimen.

6. The method according to claim 1, further comprising introducing at least one of medicaments, delivery cannula, tissue modification devices, catheters, tubes, diagnostic instruments, and pharmaceuticals and therapeutic agents.

* * * * *